United States Patent
Hendrickson

(10) Patent No.: US 6,865,512 B2
(45) Date of Patent: Mar. 8, 2005

(54) AUTOMATED MEDICAL IMAGING SYSTEM MAINTENANCE DIAGNOSTICS

(75) Inventor: David Hendrickson, Snohomish, WA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 114 days.

(21) Appl. No.: 10/293,430

(22) Filed: Nov. 12, 2002

(65) Prior Publication Data
US 2004/0093184 A1 May 13, 2004

(51) Int. Cl.[7] .............................................. G06F 11/30
(52) U.S. Cl. ................................. 702/183; 382/141
(58) Field of Search ............................. 702/32, 59, 60, 702/61, 62, 66–68, 80, 81, 119, 122, 123, 168, 171, 176–178, 182–185; 714/26, 37; 700/90; 382/141; 600/437

(56) References Cited

U.S. PATENT DOCUMENTS

| | | | |
|---|---|---|---|
| 5,062,055 A | * 10/1991 | Chinnaswamy et al. | .... 702/182 |
| 5,107,499 A | 4/1992 | Livor et al. | |
| 5,195,095 A | 3/1993 | Shah | |
| 5,463,768 A | * 10/1995 | Cuddihy et al. | ............... 714/37 |
| 6,167,352 A | 12/2000 | Kanevsky et al. | |
| 6,353,445 B1 | 3/2002 | Babula et al. | |
| 6,377,162 B1 | 4/2002 | Delestienne et al. | |
| 6,381,557 B1 | 4/2002 | Babula et al. | |
| 6,501,849 B1 | * 12/2002 | Gupta et al. | ................. 382/141 |
| 6,524,245 B1 | * 2/2003 | Rock et al. | ................. 600/437 |
| 6,543,007 B1 | * 4/2003 | Bliley et al. | .................. 714/26 |
| 6,574,518 B1 | * 6/2003 | Lounsberry et al. | .......... 700/90 |
| 6,622,264 B1 | * 9/2003 | Bliley et al. | .................. 714/26 |
| 6,643,801 B1 | * 11/2003 | Jammu et al. | ................. 714/37 |
| 6,656,119 B2 | * 12/2003 | Sasaki et al. | ............... 600/437 |

* cited by examiner

Primary Examiner—Marc S. Hoff
Assistant Examiner—Mohamed Charioui
(74) Attorney, Agent, or Firm—W. Brinton Yorks, Jr.

(57) ABSTRACT

A medical imaging system diagnostics package includes the ability to analyze operator usage data to detect aspects of the manner in which the system is used which may be a source of operating problems. Detecting problems arising from the manner in which the system is used can reduce the number of "no trouble found" repair calls and can often be permanently resolved by additional operator training in the use of the system. The diagnostic package includes the ability to assess the effects of software aging by analyzing the status of components of the medical system which are used by software such as registers, memory and disk drives. The results of this analysis can be used to improve software performance which is degraded but not failing completely such as system slowdowns and lengthened response times.

7 Claims, 14 Drawing Sheets

FIG. 6a

> ? What seems to be the problem?
> ○ Monitor
> ○ Scanhead
> ● Ultrasound Machine
> ○ Network
>
> [Submit] [Reset]

FIG. 6b

> ? How is a system problem indicated?
> ○ Degraded Preformance
> ● Error Banner
> ○ Inconsistant Behavior
>
> [Submit] [Reset]

FIG. 10

| dvsProblemRS | |
| --- | --- |
| /DVS/Rule Set | |
| Rules to determine a problem | | single_value

| conditions | value |
| --- | --- |
| sysProblemRS = prblm_sysProblemRS_DVS and qtn_sysProblemRS_BootupSeqCheck = "No" and (qtn_dvsProblemRS_Powered = "No" or qtn_dvsProblemRS_NTStart = "No") | prblmDVSHardware |
| sysProblemRS = prblm_sysProblemRS_DVS and qtn_sysProblemRS_BootupSeqCheck = "Yes" and qtn_dvsProblemRS_Powered = "Yes" and qtn_dvsProblemRS_NTStart = "Yes" | prblmDVSSoftware |
| sysProblemRS != prblm_sysProblemRS_DVS | prblm_dvsProblemRS_NotDVS |
| default | prblm_Unknown |

AUTOMATED MEDICAL IMAGING SYSTEM MAINTENANCE DIAGNOSTICS

This invention relates to medical diagnostic imaging systems and, in particular, to medical diagnostic imaging systems which can be automatically maintained to prevent system failures.

Medical imaging systems including modalities such as MRI, CT, nuclear imaging, and ultrasound represent significant investments for hospitals, clinics, and medical research institutions. As such, the facilities owning these systems usually try to make full utilization of them. System failures and breakdowns will interrupt the workflow of these systems and reduce their utilization. For this reason most manufacturers strive to provide effective periodic maintenance routines and responsive repair service. The periodic maintenance of these systems should detect potential failures before they occur, and in the event of a failure the repair service should rapidly identify and fix the problem.

Periodic maintenance procedures for imaging systems generally address the operability and state of components, modules, software, and other elements of the system itself. Factors such as voltages, temperatures, and speeds of performance are characteristics of system components which can be measured and analyzed in a periodic maintenance procedure and the results used to predict developing problems. However, system users often report problems with a system that periodic maintenance does not or cannot predict. Frequently components or modules are replaced by a repairman and returned to a repair facility where no trouble is found with the parts. In many such instances, the problems are not due to failures of the system itself, but result from incorrect use of the system or of the results it produces. Accordingly, it would be desirable for a periodic maintenance procedure to identify problems related to how the system is used, in addition to potential failures of system components.

In accordance with the principles of the present invention, a medical imaging system diagnostics package includes the ability to analyze operator usage data to detect aspects of the manner in which the system is used which may be a source of operating problems. Detecting problems arising from the manner in which the system is used can reduce the number of "no trouble found" repairs and can often be permanently resolved by additional operator training in the use of the system.

In accordance with a further aspect of the present invention, a medical imaging system diagnostics package includes the capability to monitor and analyze system characteristics which are indicative of software aging. Software aging can give rise to system problems which are not hard system failures, but degrade system performance such as performance slowdown and runtime error messages and crashes. In accordance with another aspect of the present invention, a maintenance system identifies software aging problems and presents the user with a procedure to address a software aging problem.

In the drawings:

FIGS. 6a–6d illustrate interactive imaging system diagnostics which elicit qualitative system information in accordance with the principles of the present invention;

FIG. 10 illustrates a display screen used to input logic rules for an imaging system diagnostics processor employing artificial intelligence.

Figure 1:
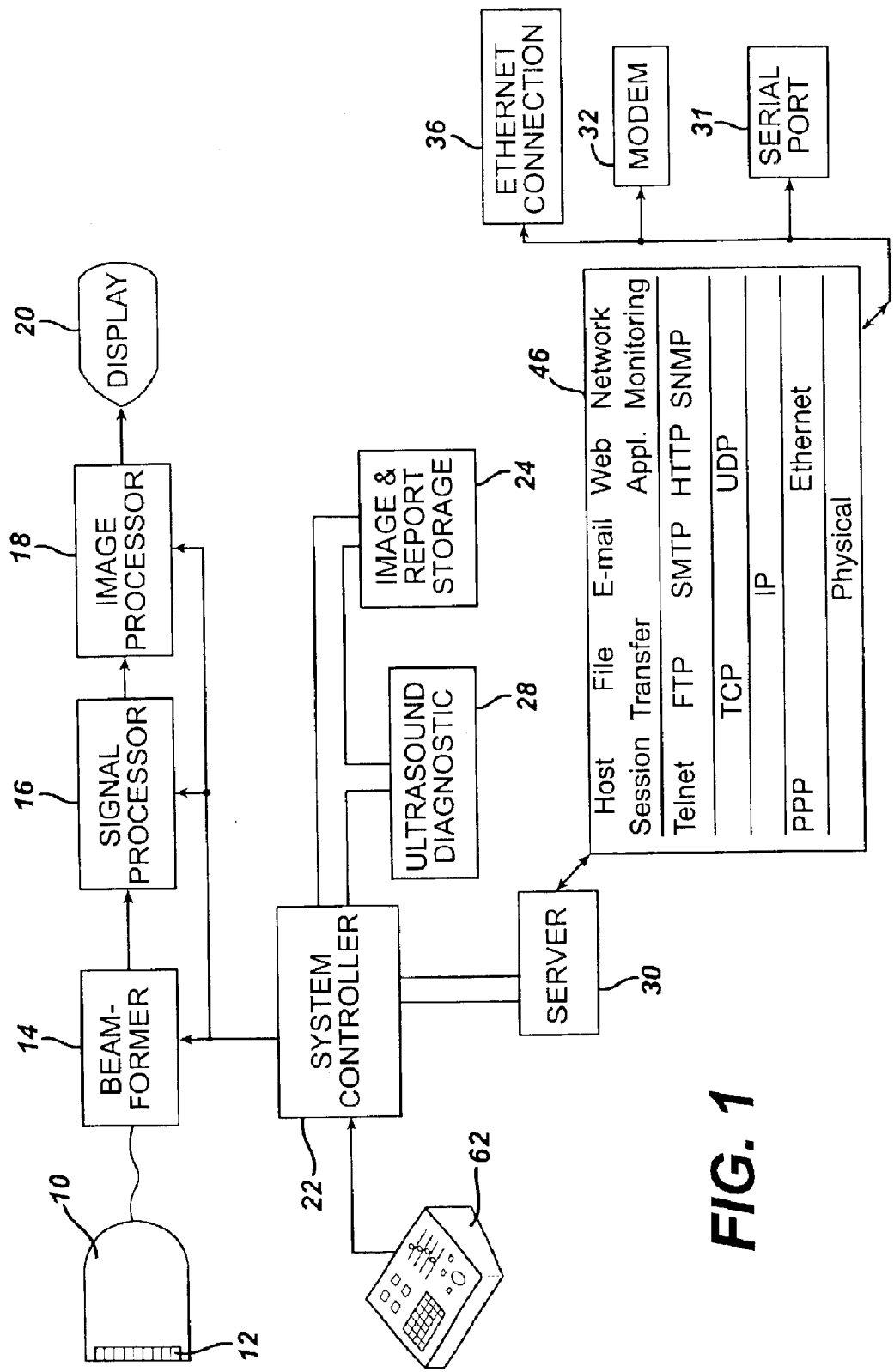
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. At the top of the drawing is the signal path of a typical ultrasound system, including a probe 10 with an array transducer 12 which transmits and receives ultrasound signals over a two or three dimensional imaging field, a beamformer 14 which processes the signals from the elements of the array transducer to form coherent echo signals, an ultrasound signal processor 16 which processes the echo signals by for example filtering, detection, Doppler processing or other processes, an image processor 18 which processes the signals into a display format, and a display 20 on which the ultrasound image or data are displayed. The operation of these components is coordinated by a system controller 22. The operation of the ultrasound system is directed by user controls 62 coupled to the system controller. The system controller 22 can store images and diagnostic reports on storage device 24. The system controller also has access to ultrasound diagnostics 28 for the performance of diagnostic maintenance and repair of the ultrasound system as described more fully below.

Figure 2:
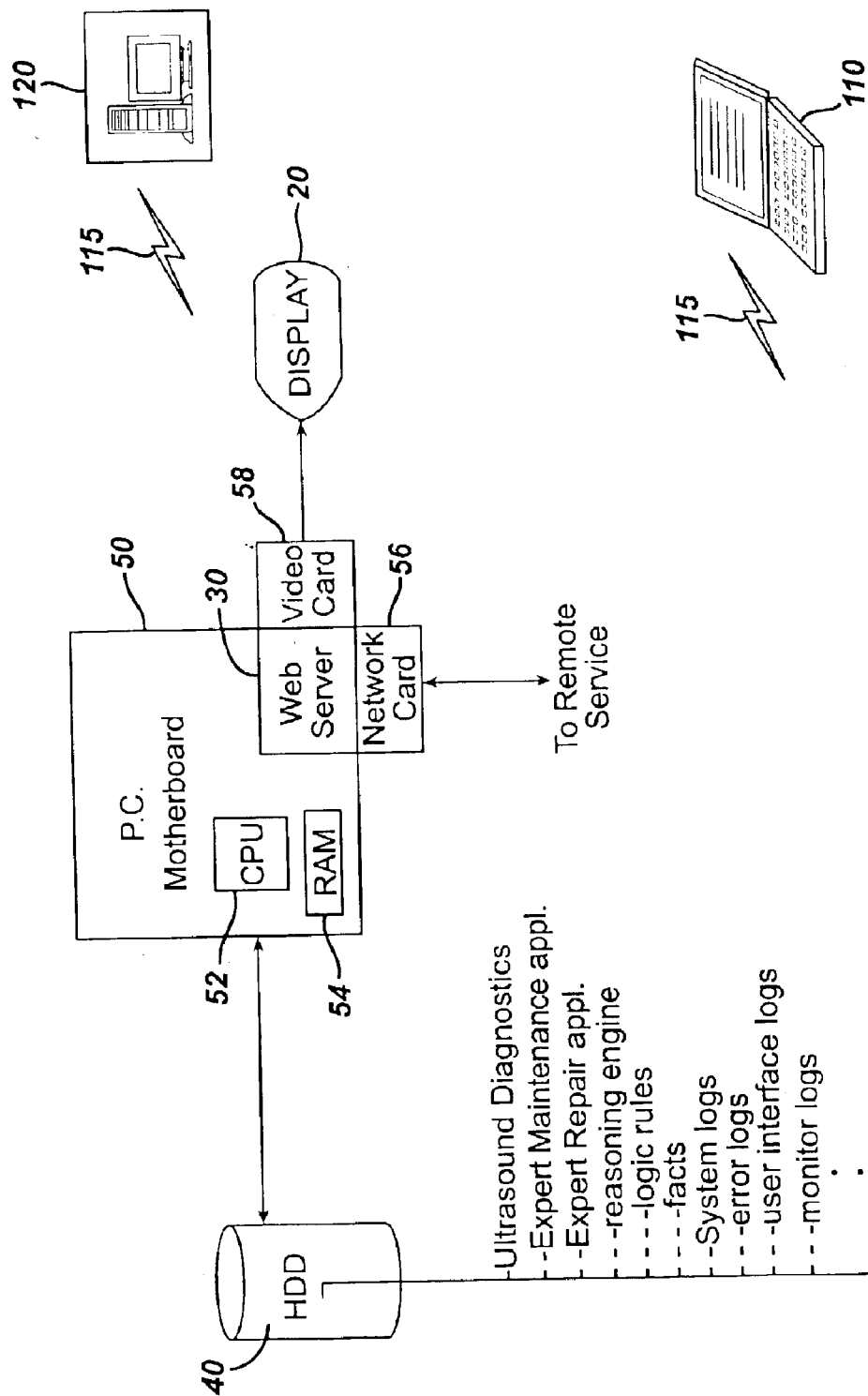
FIG. 2 illustrates in block diagram form further details of the controller and ultrasound diagnostics portions of the system of FIG. 1.

The ultrasound system includes a number of devices for the storage and communication of data such as a hard disk drive 40 which is shown in FIG. 2, and may include other peripheral devices such as, a magneto-optical disk, a CD-R drive, and/or a floppy disk drive. Some or all of the capacity for the image and report storage 24 and for storing ultrasound diagnostics 28 may be provided by these devices. The ultrasound system can also send and receive information from external sources by way of a server 30. The server communicates through a stack of protocols 46, which illustrates some of the more universal communications protocols which may be employed. At the upper layer of the stack 46 are applications protocols for host sessions, file transfer, e-mail, Web applications and network monitoring. At the next level of the stack are Telnet, FTP, SMTP, HTTP and SNMP presentation protocols. At the third layer are the TCP and UDP protocols, and at the next layer is the IP protocol. At the fifth layer are PPP and Ethernet protocols, and at the bottom of the stack is the physical layer which connects to external communication devices. Several communication devices are shown in the embodiment of FIG. 1, including a serial port 31, a modem 32, and a network (Ethernet) connection 36. This array of communication protocols and devices enables the ultrasound system to connect directly to other devices by way of proprietary or public point-to-point networks, by phone lines, and/or over the Internet and the World Wide Web.

In FIG. 2, portions of the ultrasound system of FIG. 1 are illustrated in further detail. The system controller 22 includes a computer motherboard 50 which includes a CPU 52 and random access memory (RAM) 54. The CPU executes preventive maintenance (PM) and repair diagnostic applications stored on a disk drive 40. The CPU also executes other applications running on the ultrasound system. Some of the programs and data files of the diagnostic application stored on the disk drive 40 are listed in the drawing under the heading Ultrasound Diagnostics, including an Expert Maintenance application which conducts PM, an Expert Repair application running a reasoning engine and utilizing logic rules and facts, and System logs including files such as error logs, user interface logs, monitor logs, service logs, and temperature/voltage logs. These programs and application are discussed more fully below. The motherboard 50 also operates a Web server 30 which, in a preferred embodiment, is connected to a video card 58 and a network card 56. The video card enables the Web server to display Web pages on the system display 20. The video card may also be used in a constructed embodiment to display diagnostic images and information on the display 20 which have been produced by the image processor 18. The network card enables the Web server to communicate through a network 115 with a serviceperson having remote access to the ultrasound system as described in U.S. patent application Ser. No. 09/534,143 as indicated by remote diagnostic device 110, or with a service center 120 such as might be operated by the manufacturer of the ultrasound system. By connecting the Web server to both the network card and the video card, a remote serviceman can be looking at the same screen display as the imaging system operator viewing the display 20.

Figure 3:
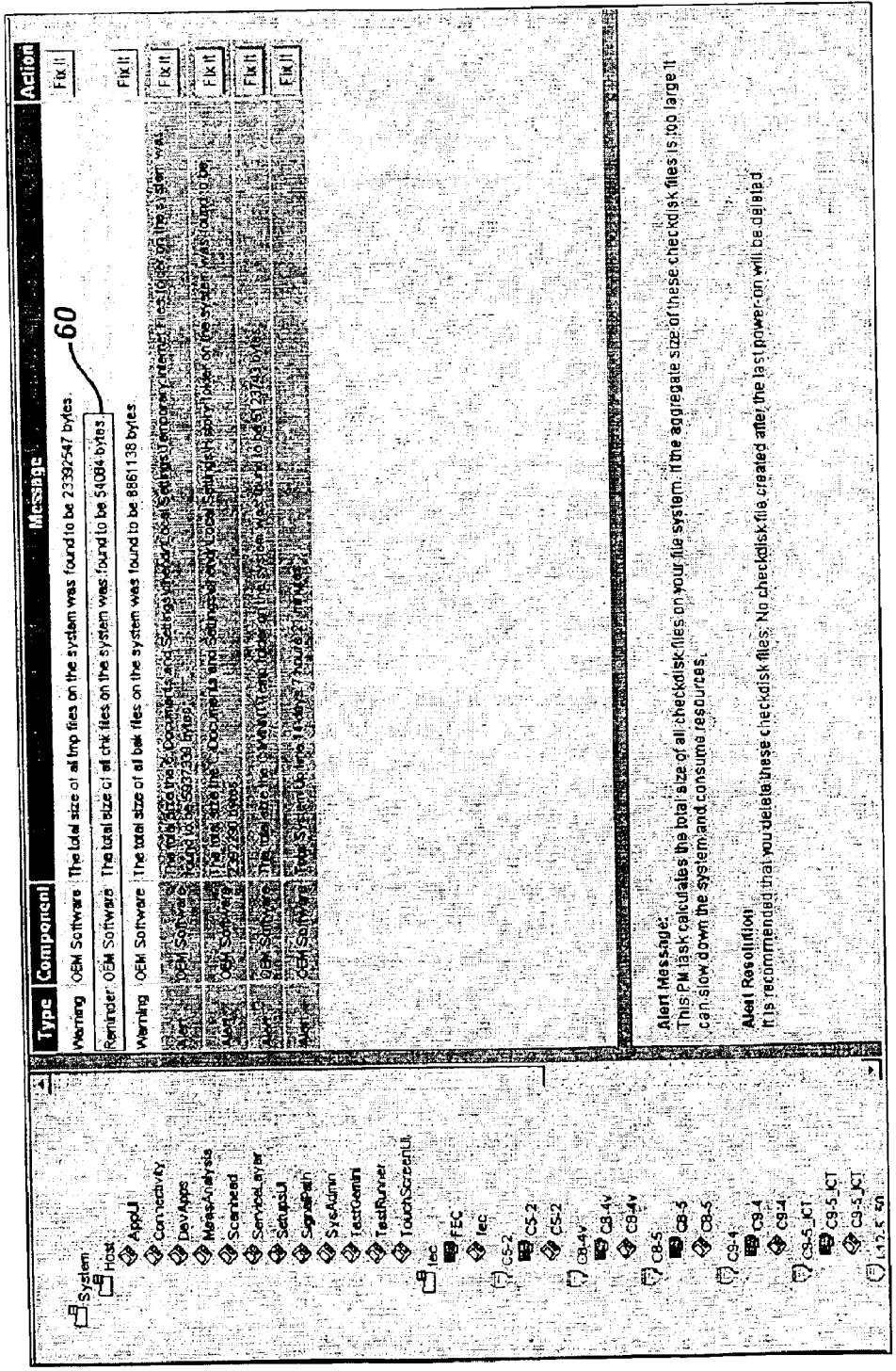
FIG. 3 illustrates one example of the results of periodic maintenance diagnostics conducted in accordance with the principles of the present invention.

In accordance with the principles of a first aspect of the present invention, the ultrasound diagnostics include a preventive maintenance system referred to herein as an Expert Maintenance application. The Expert Maintenance application preferably resides on the ultrasound machine and is executed when the ultrasound machine enters the diagnostics mode. The Expert Maintenance application is automated and can be initiated by the ultrasound system operator, by an on-site repairman, by a repairman with remote access, or by a repair center with remote access as shown in FIG. 2. The Expert Maintenance application can also be initiated by the imaging system itself during off-hour self-maintenance. The Expert Maintenance application analyzes system parameters according to a set of rules, some of which may be user defined as discussed below. In a constructed embodiment, the Expert Maintenance application analyzes the ultrasound system and reports reminders for non-critical problems, or alerts for problems that could cause system failures. A report of the maintenance analysis is presented to the user as shown in FIG. 3 to allow the user to choose which reminders and alerts to resolve.

In accordance with the principles of a further aspect of the present invention, preventive maintenance is applied to both hardware and software components. Hardware maintenance is defined as those activities regularly performed to a physical device to prevent developing problems from becoming failures. Examples of such maintenance include replacing overheating components, cleaning corroded electrical contacts, or reseating loose electrical connections. Techniques for sensing these types of problems are well known, and include monitoring temperature sensors, electrical impedances, and applied voltages, and need no further elaboration. The monitored parameters are recorded by the Expert Maintenance application and presented to the user in the report. The severity of the condition is indicated to the user (reminder, alert, warning) and the user or machine can then take appropriate action.

Software maintenance, on the other hand, is defined as those periodic activities performed on software to reduce or eliminate the effects of software aging. This may be contrasted with software failures such as software crashes or software which does not run or does not run properly, all of which are "hard" failures and many of which require the attention of a serviceman to repair or replace the faulty software. Software aging can lead to software failures and software maintenance is intended to prevent such failures. Software aging can be detected by identifying the effects of software aging, examples of which include memory leaks, unreleased file locks, data compaction, storage space fragmentation, and accumulation of round-off errors which can cause poor system performance or, ultimately, system failure. Examples of responses to these detected conditions can be as simple as rebooting the ultrasound machine, more involved such as defragmenting the system disk drive, or as complex as replacing old software or adding system resources. The effects of software aging if left untreated, can impact the diagnostic capability of the system through greater downtime, degraded system performance, or reduced system dependability.

The Expert Maintenance application can analyze numerous software operating parameters retrieved in real time or observed in machine logs and reports the results of this analysis to the user for recommended action. Some of the parameters which are analyzed in a constructed embodiment include the following:

A. The Expert Maintenance application analyzes the number of temporary files (*.tmp) created prior to the last time the system was booted up. This number can be compared to a maximum desired number of temporary files set by the user.

B. The Expert Maintenance application analyzes the number of backup files (*.bak) created prior to the last time the system was booted up. This number can be compared to a maximum desired number of backup files set by the user.

C. The Expert Maintenance application analyzes the number of disk-check lost files (*.chk) created during the previous scandisk operation. This number can be compared to a maximum desired number of lost files set by the user.

D. The Expert Maintenance application analyzes the number of Web browser total history files. This number can be compared to a maximum desired number of history files set by the user.

E. The Expert Maintenance application records the hard drive's free storage from the operating system and alerts the user if the free space is below a given size such as 10% of the total disk size.

F. The Expert Maintenance application analyzes the fragmentation of the hard drive and alerts the user if the file fragmentation exceeds a predetermined amount such as 10%.

G. The Expert Maintenance application analyzes the number of committed bytes to determine if the number exceeds the amount of physical RAM.

H. The Expert Maintenance application analyzes the number of page reads per second to determine whether the system is loading more programs into virtual memory than can be handled efficiently.

I. The Expert Maintenance application analyzes the total bytes received per second on a system network to see if the number is in excess of a steady-state level, which indicates excess utilization of system bandwidth.

J. The Expert Maintenance application analyzes the disk access time and alerts the user if the disk access time exceeds a certain percentage.

These are only a few of the possible techniques for detecting software aging. None of these conditions are symptomatic of immediate system failure, but each one of them indicates a developing condition that can lead to a problem or a perceived problem. One problem that may be perceived by the system operator is that the system is operating slower than it has in the past. While not a hard failure, this is a problem that could result in a service call but which can be often be resolved by the Expert Maintenance application. FIG. 3 illustrates the detection of factors which may be causing or could lead to a perceived system slowdown condition. FIG. 3 illustrates a typical report shown on the display screen at the conclusion of the execution of the Expert Maintenance application. The window on the left side of the screen shows modules that may be examined by the Expert Maintenance application, including a series of System modules, the front end controller (FEC) of the ultrasound machine, and a number of ultrasound probes (C5-2, C8-4v, etc.) The upper right window shows the results of the periodic maintenance, which in this example are seen to be symptoms of software aging. The severity of the condition is indicated at the left of the window (warning, alert) and a button which will cause the condition to be resolved is presented to the right of each condition. For instance, if the user clicks on the "Fix It" button to the right of the temporary file warning at the top of the window, the system will automatically delete the temporary files created prior to the most recent system bootup. Most of the resolutions shown in this window will reduce the consumption of system resources which may be contributing to or leading up to a system slowdown condition, and could avoid the need for a service call to address the problem. While in some instances a permanent solution may only be attained by an increase in resources such as more RAM or a larger disk drive, in many instances the condition is only a temporal one which can be cured by the system operator at the end of the preventive maintenance procedure.

If the user wants more information on a result, he highlights the result as indicated by box 60. The window below then presents more detailed information about the nature of the condition and advises the user as to the problem that can arise if the condition is not resolved. A recommendation is also given in this window.

Figure 4:
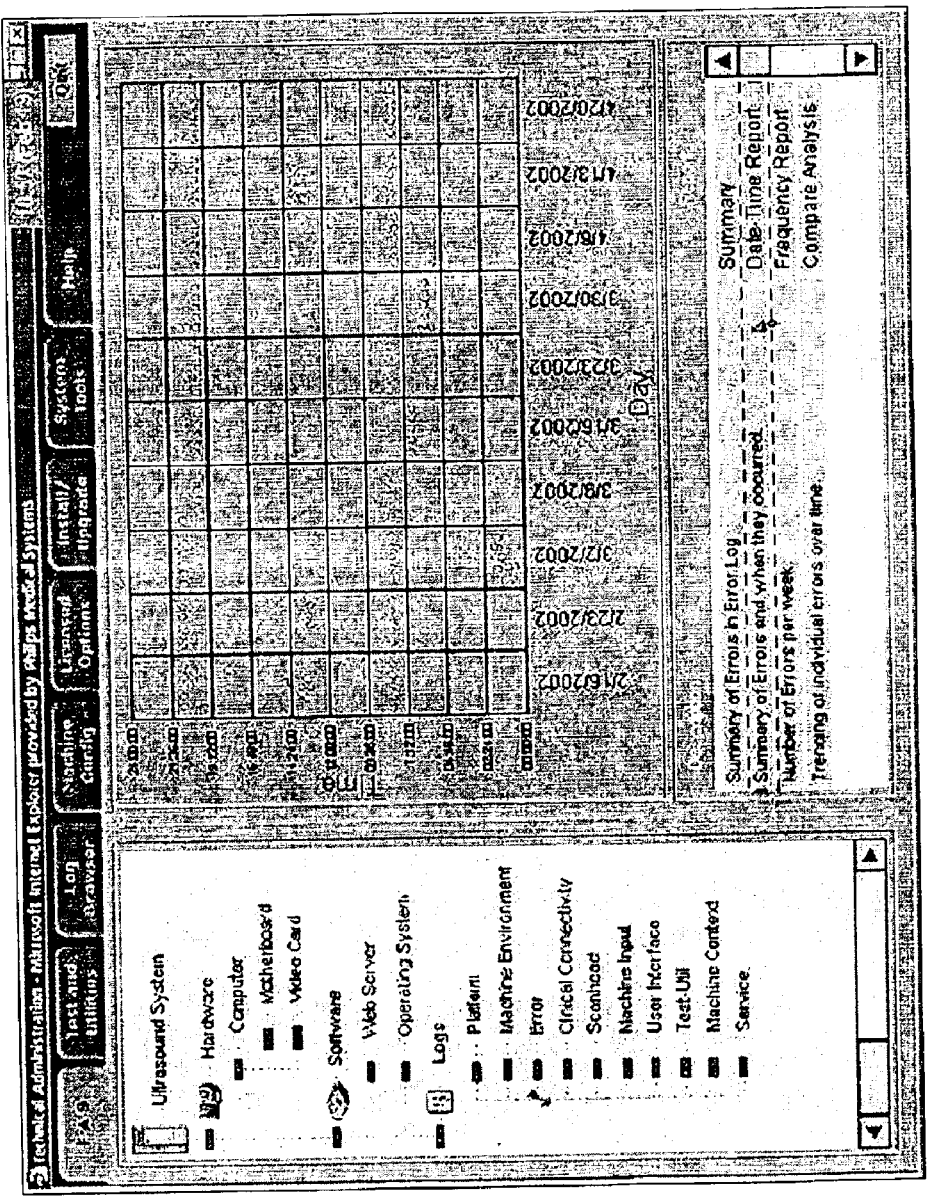
FIG. 4 illustrates the presentation of system usage data in the form of a scattergram.
Figure 5:
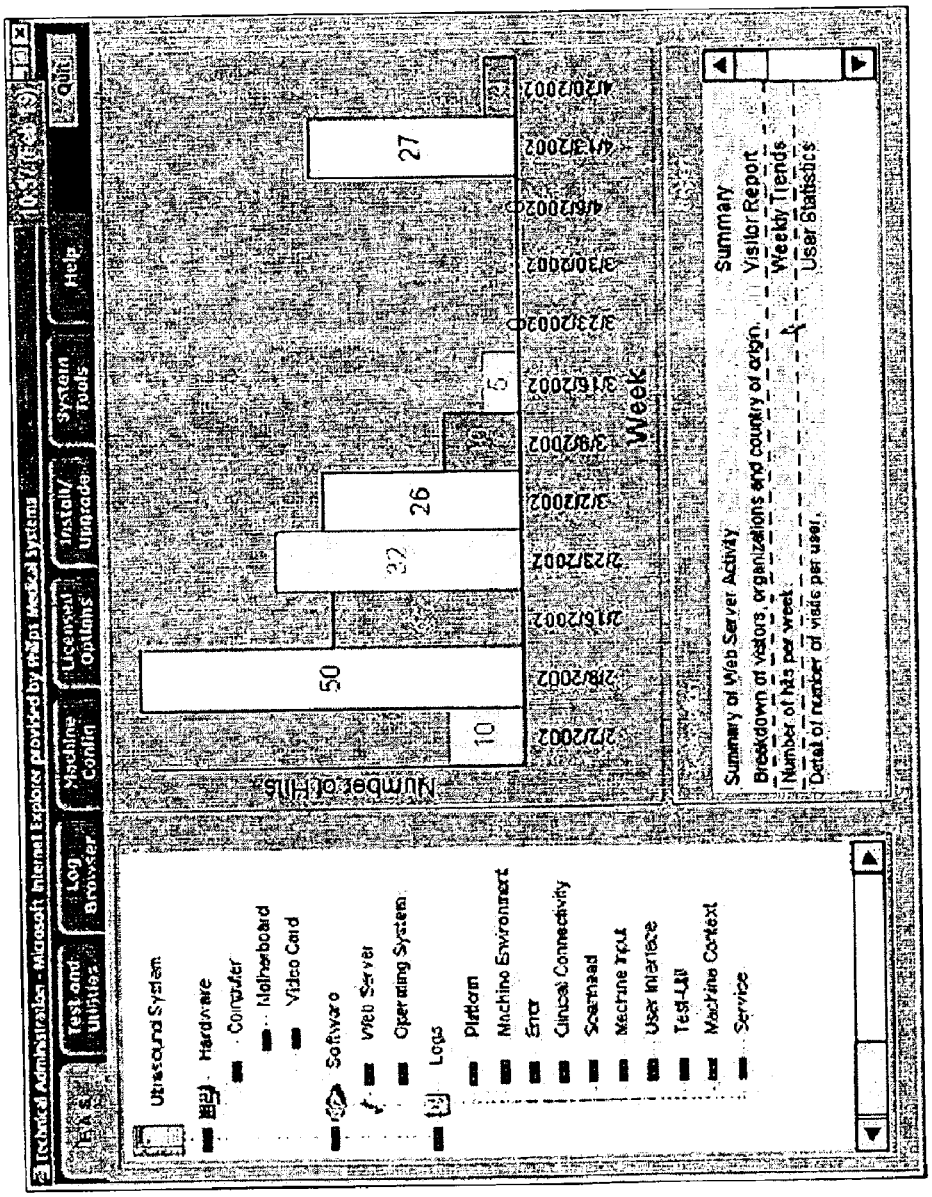
FIG. 5 illustrates the presentation of usage trend analysis in the form of a bar chart.

In accordance with the principles of another aspect of the present invention, the Ultrasound Diagnostics analyze system usage data to resolve problems. Usage data analysis may be used during preventive maintenance procedures or during repair procedures. While hard system failures are relatively easy to detect, and problems such as system slowdowns are relatively more difficult to detect, some problems are not caused by system failures at all, but by the manner in which the system is used. Many such problems can be identified and addressed through an analysis of system usage data. This data can take numerous forms and be resident in different locations on the ultrasound system. In a constructed embodiment, usage data is resident in the System logs and the error logs stored on the disk drive 40. FIGS. 4 and 5 show two presentations of system usage data as a function of time. The left window of FIGS. 4 and 5 shows a number of System logs typically maintained on the ultrasound system. The windows on the right side of FIG. 4 show a scattergram of usage data over a period of two months, with the bottom window identifying the usage data used in the scattergram. In this example error events in the error log are plotted as a function of the time of day they occurred over the two month period. The scattergram shows error events logged virtually every day between 7 am–8 am. These are probably conditions logged when the ultrasound system was booted up each morning. Similarly, there is a fairly uniform occurrence of daily events between 1900 hrs. and 2100 hrs., probably due to periodic maintenance performed automatically during off-hours each evening. But clusters of aperiodic events are also seen in the scattergram. For instance, there is a cluster of events which occurred between 12 noon and 1424 hrs. during the week of April $13^{th}$ (Apr. 13, 2002). This clustering would prompt an investigation of what the ultrasound machine was doing at those times and dates. What type of exams were conducted then? What operating modes were used? Who was operating the system at those times?

Usage information may also be presented in barchart form as shown in FIG. 5, in which trends may be observed. This graph shows the number of error events occurring each week over a two month period. These results would prompt questions such as: What was the usage of the ultrasound system during the week of February 9, when incidents were at their highest? What was the usage of the ultrasound system during the period March 23–March 12, when incidents were at their lowest?

The identification of trends and patterns in the machine data can be observed visually and identified by a human by way of the machine's diagnostic reports, or this knowledge can be encoded into the machine's repair/maintenance system where the trends and patterns can be automatically identified either exactly as they were identified by a human or within a user definable similarity factor.

The answers to the inquiries prompted by these presentations of usage data often lead to problems and errors arising when the ultrasound machine was not used properly. Frequently they point to use by operators who have had insufficient system training or little system experience. Thus, instead of making a service call which will only lead to "no trouble found" with the machine, such problems may often be resolved by providing increased training to the sonographers operating the ultrasound machine.

This response will not only benefit the institution and manufacturer by reducing service calls; it can also help the institution become more skilled and competitive. For example, a clinic may communicate its usage data to a service center of the manufacturer where it can be compared with the usage data of other system owners. The usage data from one clinic may show a considerably higher level of error events than that of a similar clinic doing similar exams across town, across the country, or on the other side of the globe. As a result, the service center can assist the clinic in examining its workflow and system usage in comparison with that of other institutions. Through increased training and/or process improvement, the clinic can improve its efficiency and system utilization, and as a consequence the level of service and healthcare benefits it provides.

Figure 6C:

In accordance with another aspect of the principles of the present invention the diagnostics package includes an interactive repair system which queries the user and provides guidance which enables the user to resolve ultrasound system problems without the intervention of a serviceman. The interactive repair system may also be used by service personnel, of course. The interactive repair system is able to acquire qualitative information from the user about the state of the ultrasound system. It is then able to combine this qualitative information with quantitative information it acquires automatically and analyzes both types of information to arrive at a recommended repair strategy. Several query screens of an embodiment of an interactive repair system are illustrated in FIGS. 6a–6d. When the user enters the interactive repair mode, the repair system first inquires as to the nature of the problem, as shown in FIG. 6a. What area of the ultrasound system seems to have the problem? the user is asked. A number of choices are presented from which the user can make a selection. In this example the user clicks the "Ultrasound Machine" choice and then clicks the "Submit" button to enter his selection. If the user clicks a selection and changes his mind, he can click the "Reset" button to clear the previous choice, and can click the "Reset" button twice if he wants to go back to a previous question.

Figure 6D:

After the user indicates that the problem seems to be with the ultrasound machine in this example, he is asked to give further information on the evidence of the problem, as shown in FIG. 6b. The user is asked, for instance, whether the problem seems to be one of inconsistent behavior or degraded performance, the nature of which can be subjective. In this example the user has seen an error banner, and chooses this as the answer to submit. In response to this answer, the repair system asks the user which error banner he has seen, as shown in FIG. 6c. Here, the user is given a pull-down list from which to make a selection. The user pulls down the list and submits the appropriate banner number. When the repair system receives the banner identity in this example, it then looks for a known correlation between the chosen banner and another system operation, in this case a prior illegal shutdown. In FIG. 6d the user is posed the question of whether there was an illegal shutdown prior to the error. The user can make a selection of "Yes" or "No," or can click on "Check Logs," which prompts the repair system to automatically search the System logs stored on the disk drive 40 to automatically answer the question.

Figure 7:
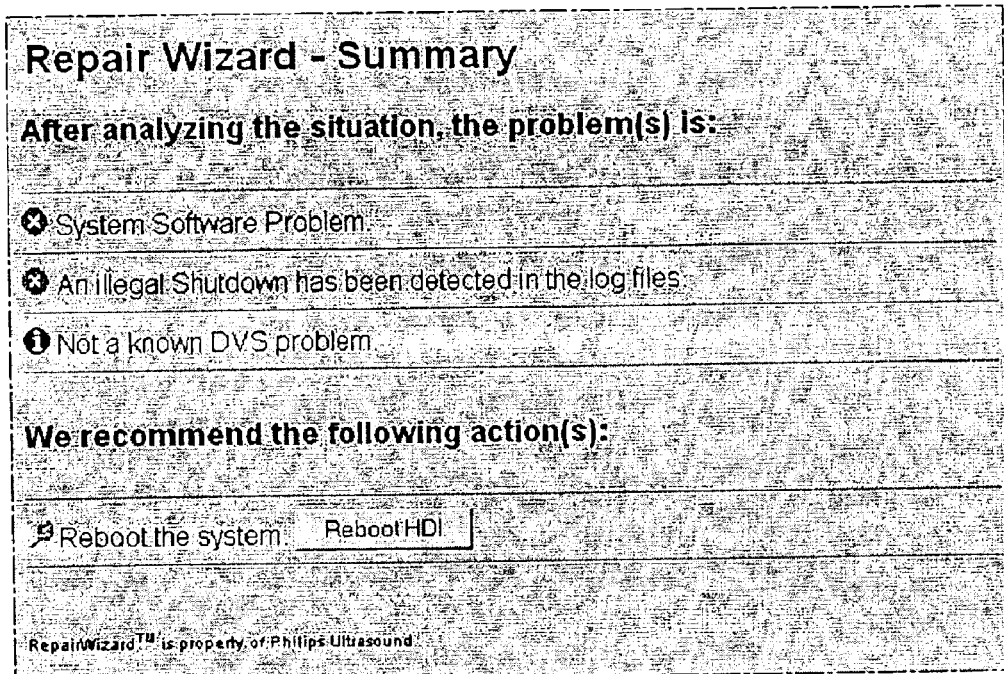
FIG. 7 illustrates an example of the presentation of the results of interactive imaging system diagnostics.

After the queries have ended and the repair system has acquired the needed relevant information, the repair system presents its conclusions and recommended course of action. It is possible that the entered information does not point to a definitive repair procedure, or points to a repair requiring a serviceman, in which case the recommendation is given that a service call be made. In the example shown in FIG. 7, the repair system concludes that the problem is not a known digital video subsystem (DVS) problem; that an illegal shutdown was detected in the error log files; and that this is a system software problem. The user is given a recommended course of action, which in this example is to reboot the ultrasound system.

These repair activities and their outcomes are recorded and stored on the system disk drive 40. If the same problem or a similar problem occurs in the future, the repair system will have this historic information on which to base a recommended course of action. For instance, if a problem of degraded performance recurs several times in a short timeframe, the repair system may conclude that more system resources are needed to support the applications run by the user. A service call would be recommended so that a repairman could evaluate the need for upgraded RAM or a larger disk drive for the ultrasound system, which would permanently address the problem.

Figure 8A:
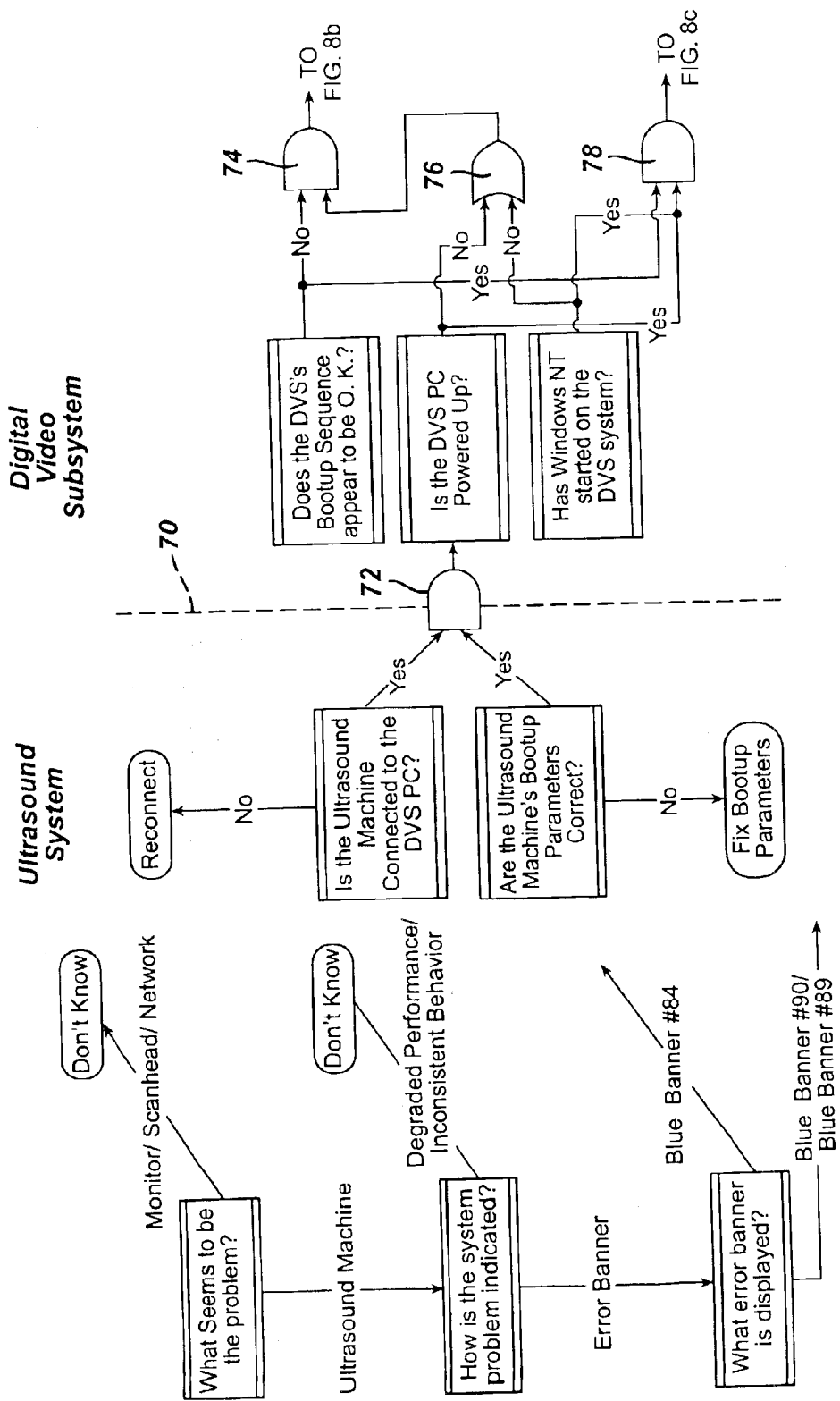
FIGS. 8a–8c illustrate a logical flowchart of the analysis of interactively acquired system diagnostic information by artificial intelligence processing.
Figure 8B:
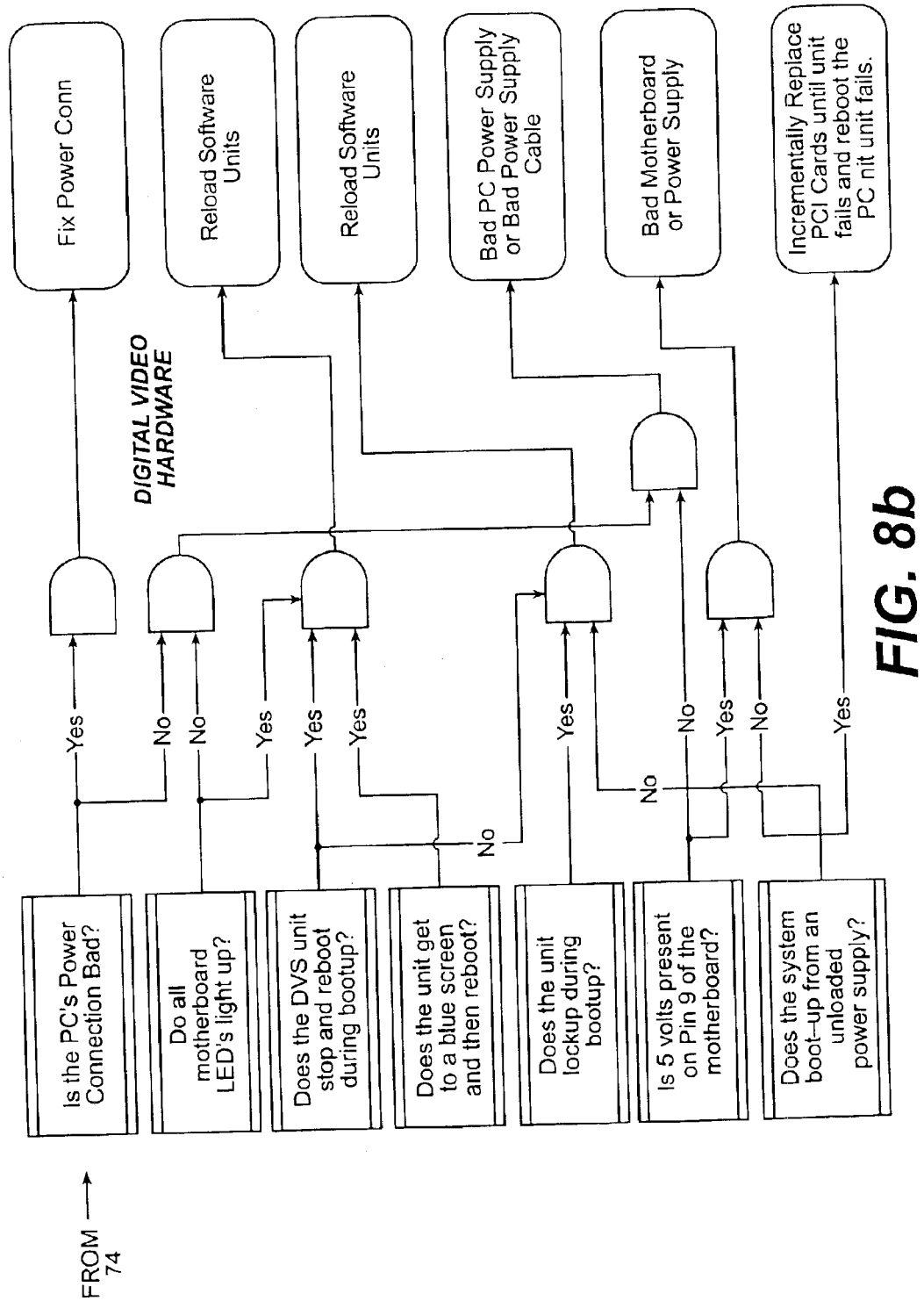
Figure 8C:
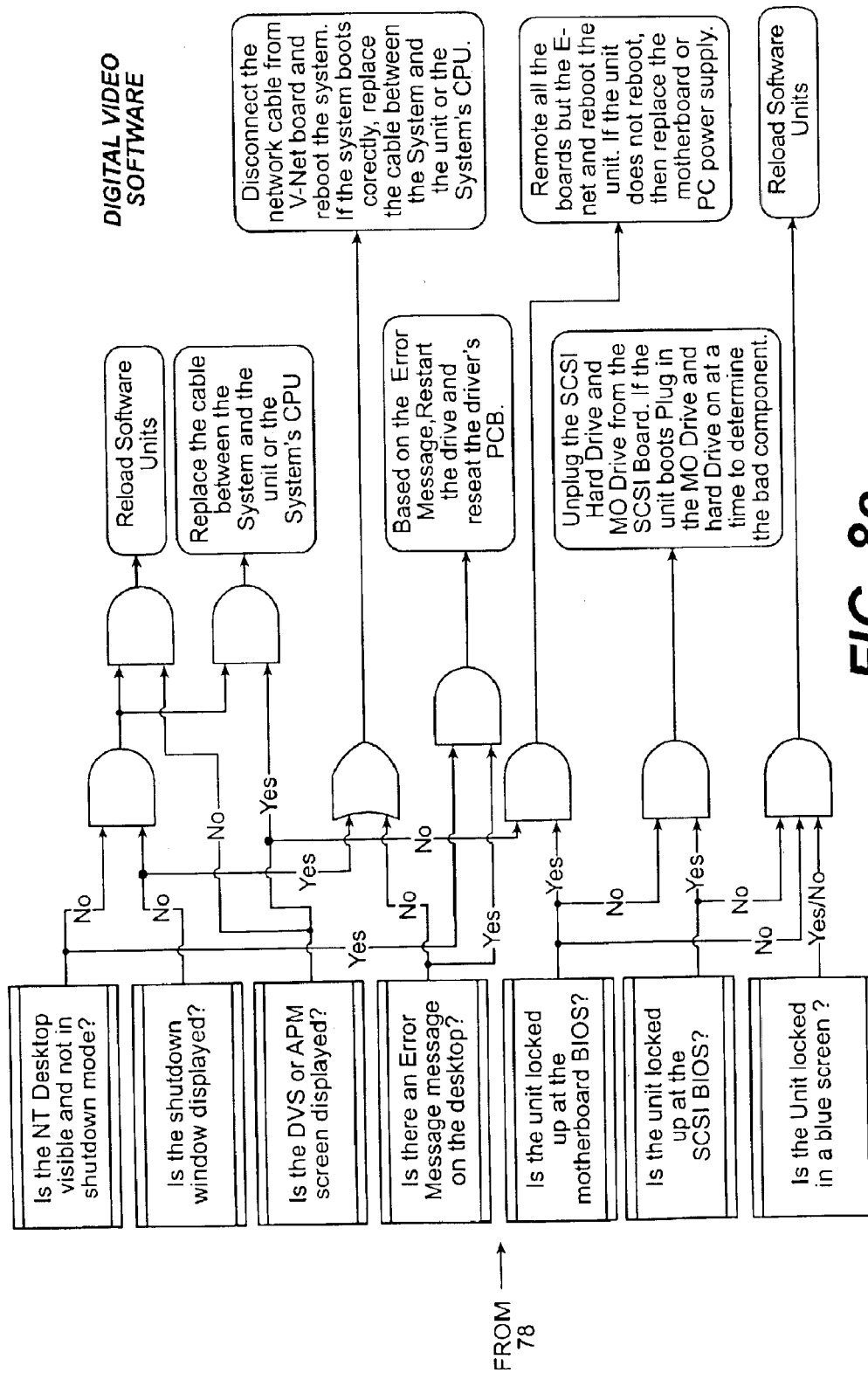

Details of the content and operation of a repair system of the present invention are shown in FIGS. 8a–8c, 9, and 10. FIGS. 8a–8c illustrate a logical flowchart of a sequence of questions and answers posed and received by the repair system when there is a problem with the digital video subsystem (DVS). In a constructed embodiment shown in these drawings the first sequence of questions to the left of the dashed line 70 elicit individual answers which lead directly to the next question. For instance, the answer that an error banner was displayed leads directly to the question of Which error banner was displayed? To the right of the dashed line 70, the logic becomes more complex, as the answers to multiple questions are needed before the next inquiry can be formulated as indicated by logic gates 72–78. For instance, the logical AND gate 74 will only produce an output if it receives a "No answer to the question to the left of the gate, and if the answer "No" is entered in response to the other two questions below, as indicated by the output of logical OR gate 76 which is coupled to an input of gate 74.

The outputs of the logic gates 74 and 78 are coupled as inputs to the processes illustrated in FIGS. 8b and 8c. While these processes show a series of questions and logical operations and may be constructed in this way, in accordance with a further aspect of the present invention these processes are performed by an inferencing or reasoning engine. An inferencing engine employs backward chaining (goal-driven strategy) to reason about a given problem, in this case, a problem with the operation of the ultrasound system. This approach relies on the assumption that the existence of a goal must be either established or refuted. This strategy is enhanced with depth-first search with backtracking. All of the rules from within a rule-set are ordered first-come-first-serve and the first successful goal encountered is the goal reported to the user. Alternatively, the inferencing engine can analyze and consider all possible outcomes, and report a list of prioritized strategies for resolving the problem In a constructed embodiment a run-time reasoning engine available from Amzi!, Inc. of Lebanon, Ohio, USA was used. The reasoning engine utilizes logic rules and facts which are stored on the disk drive 40 or which are input as answers by the user to questions posed by the system. The reasoning engine does not look simply at the answer to the previous question, but analyzes the answers provided to all of the previously asked questions, as well as other facts known to the system. The reasoning engine thus applies artificial intelligence to the information given to arrive at a conclusion and recommendation. It does this by deciding which question to pose next, and by continually analyzing all of the answers given and facts available until all of the available known valid information satisfies a series of rules which lead to a known problem and its repair solution. The benefits of this approach include the ease of implementation; rules and facts are easy to understand and are communicated naturally; outcomes can be easily explained and derived; new facts and rules can be added independent of the analysis program; and new facts and rules can be combined with previously known facts and rules to infer new knowledge.

FIGS. 8b and 8c illustrate a number of the questions which the reasoning engine may pose to the user, and a number of conclusions which may be reached by this artificial intelligence processing. Some of the recommended courses of action may be performed by the user such as reloading software units, while others such as unplugging a hard drive, replacing PCI cards, and replacing a power supply will generally require the expertise of a technician or serviceman. Thus, it is apparent that the reasoning engine may be used by either the user or the repairman to facilitate ultrasound system analysis and repair.

Figure 9:
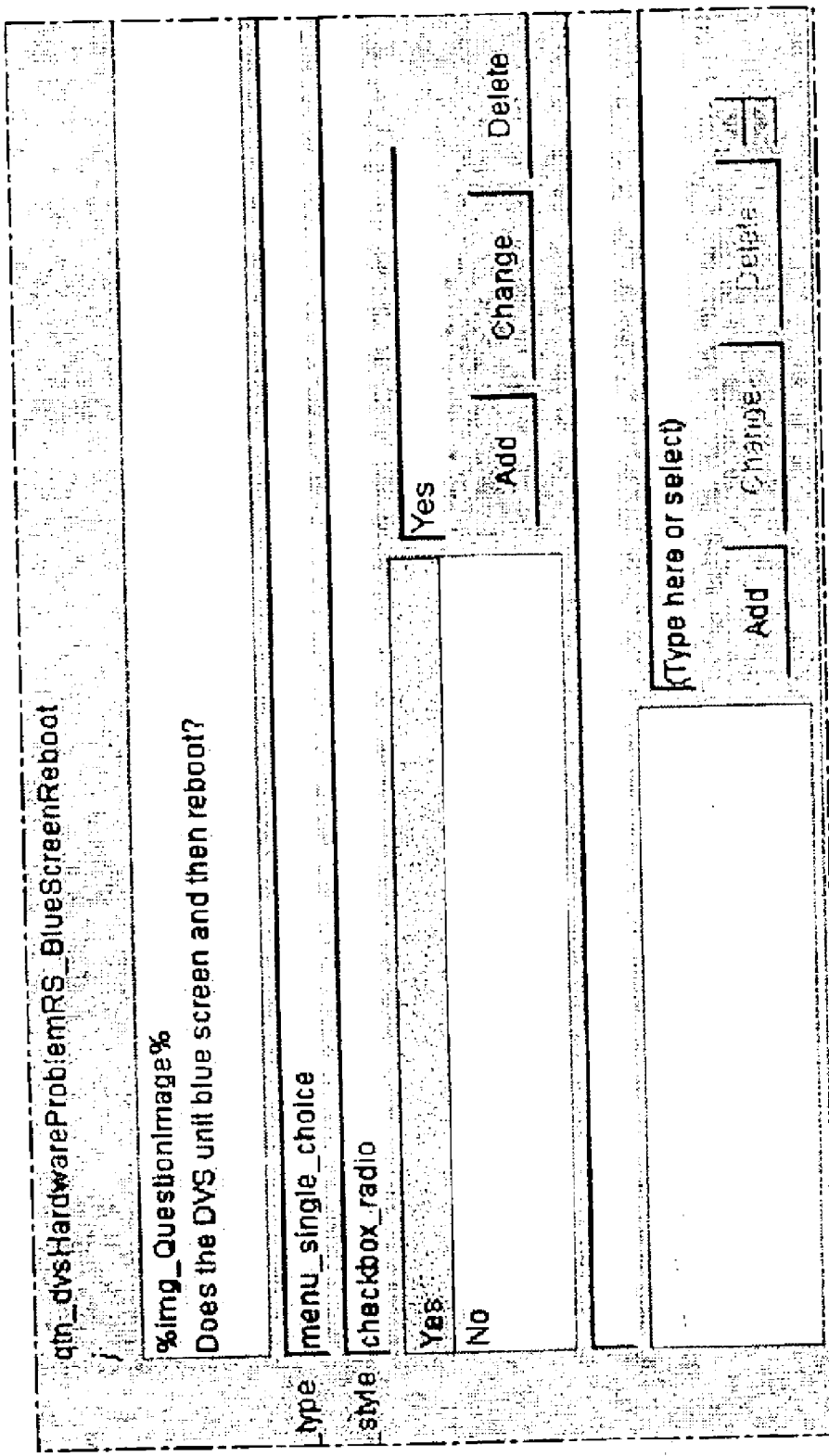
FIG. 9 illustrates a display screen used for the entry of a diagnostic query for an interactive diagnostics system.

FIG. 9 illustrates a screen from which an ultrasound system manufacturer or service technician can enter questions to be asked by an interactive repair system. A text-based programming language such as xml or Prolog is preferably used to program the questions, which enables manufacturing or repair personnel with minimal familiarity of computer programming languages to formulate and enter the questions. In the example shown the question, "Does the DVS unit blue screen and then reboot?" has been entered, to which the answers presented are "Yes" or "No."

FIG. 10 illustrates logic rules written to guide a reasoning engine in analyzing a problem. Again, a text-based programming language is preferably used for ease of programming and understanding. In this example the programmer enters in the left column the conditions which are logically present under a given condition, and in the right column the conclusions reached by the reasoning engine for the defined conditions. The reasoning engine will use logic rules such as these and facts about the ultrasound system which are stored on the disk drive 40, together with other facts and data available on the ultrasound system at the time such as those resulting from automated measurements, together with the qualitative answers entered by the user to analyze a particular problem and logically arrive at a conclusion and, if possible, a recommended course of action.

At the conclusion of an artificial intelligence-aided repair procedure, the results of the repair may be stored in a local knowledge database resident on the system or on a network accessible to the system. These results then constitute information or facts which are known to the repair system for the conduct of future repair analyses. The results of the repair may also be communicated back to a repair center 120 or downloaded by the repair center or a repairman periodically and sent to the repair center. At the repair center other repair personnel and/or the ultrasound system manufacturer may use these results produced by one ultrasound system in the repair of other, similar ultrasound systems at other locations. The information can also be communicated to these other systems as facts to be considered by their reasoning engines as they analyze problems on their own systems. The information can also be entered into a manufacturer's database and used in the design and production of future ultrasound systems.

Figure 11:
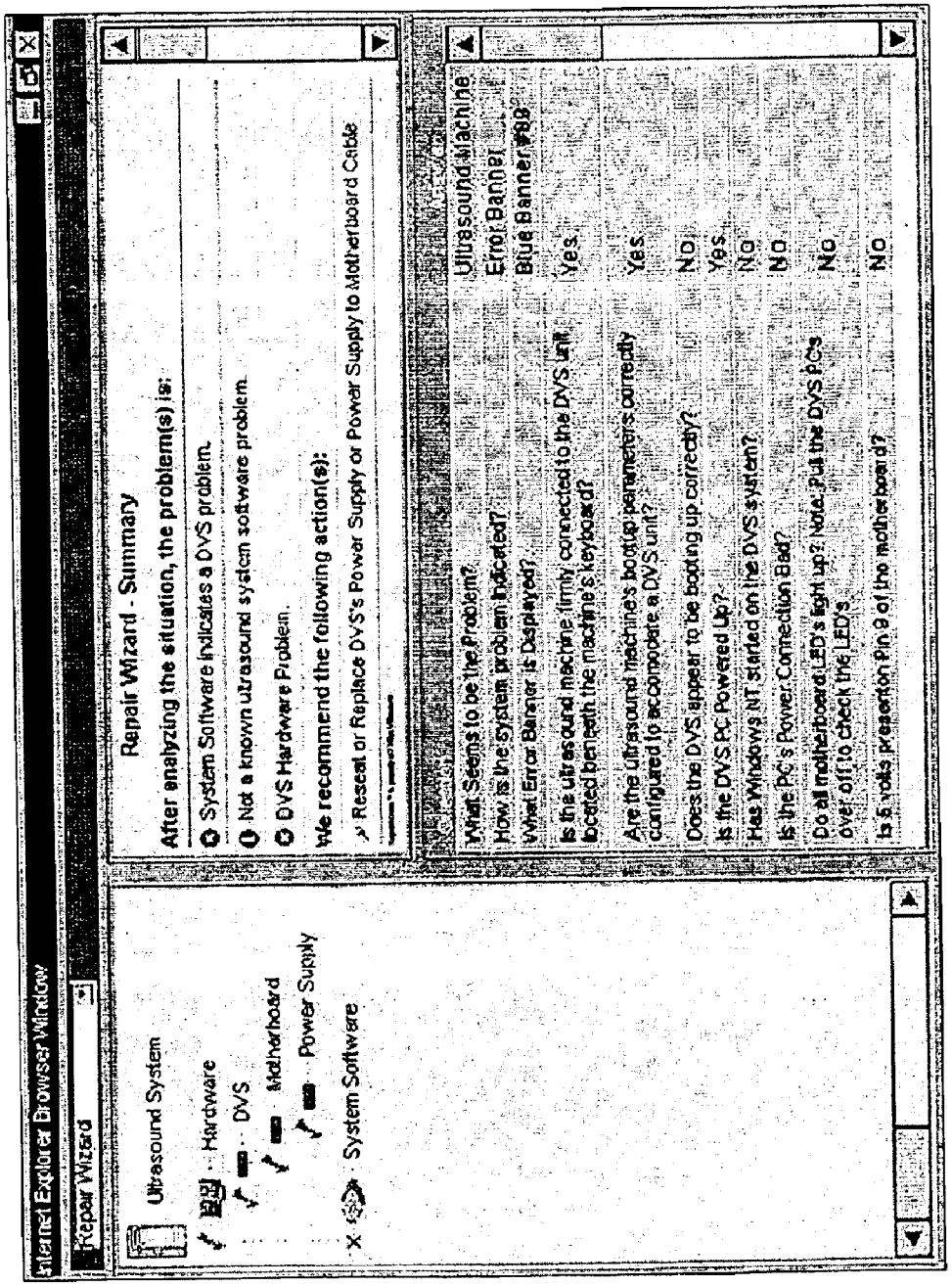
FIG. 11 illustrates another embodiment of an interactive imaging system diagnostics package of the present invention.

Another embodiment of a repair system of the present invention is illustrated by the display screen of FIG. 11. This screen includes a box presenting the results of a repair diagnosis and a recommended repair strategy at the upper right. In the box on the left side of the screen is a tree of the system architecture which may be diagnosed and repaired by the automated repair system. The box at the lower right of the screen presents a recapitulation of the questions posed by the system and the answers entered by the user, on which the repair recommendation was based. This recap box gives the user the ability to review the answers he gave to verify that the proper answers were entered. If the user sees an answer that he wishes to change, he does so and the automated repair system then logically analyzes the data as augmented by this different input to again arrive at a conclusion and recommendation.

One skilled in the art will recognize that an automated medical imaging system repair system of the present invention may be contained in a serviceman's repair device such as the laptop repair system described in the aforementioned U.S. patent application Ser. No. 09/534,143, or may be integrated into the medical imaging system itself. When the repair system is integrated into the medical imaging system, much of the repair expertise of a skilled serviceman is encoded into the imaging machine itself, where it is then available at the user's location for use by the clinical operator of the system or by a repairman making an on-side call to the user's location.

What is claimed is:

1. A medical diagnostic imaging system, including hardware components operated by software stored on and utilized by the system to conduct a diagnostic imaging procedure, and an imaging system maintenance system comprising:

a maintenance program, responsive to operator initiation and coupled to hardware components of the imaging system, which receives inputs from components interacting with the software stored on and utilized by the system for the detection of conditions of software aging which degrades system performance; and a display responsive to the maintenance program which presents the results obtained by the maintenance program.

2. The medical diagnostic imaging system of claim 1, wherein the display is responsive to the maintenance program to recommend a course of action to resolve a software aging problem.

3. The medical diagnostic imaging system of claim 2, wherein the display is responsive to the maintenance program to recommend adding system resources.

4. The medical diagnostic imaging system of claim 2, wherein the display is responsive to the maintenance program to recommend rebooting the system to address a software aging condition.

5. The medical diagnostic imaging system of claim 2, wherein the implementation of the recommended course of action improves the system response time.

6. The medical diagnostic imaging system of claim 2, wherein the display is further responsive to the maintenance program to present an operator selection which, when selected, at least partially remedies a software aging condition.

7. The medical diagnostic imaging system of claim 1, wherein the conditions of software aging include one or more of the number of temporary files; the number of backup files.; the number of saved lost files; the number of browser history files; the amount of hard drive free storage; hard drive fragmentation; the number of committed bytes; the number of pages read per second; the total number of bytes received per second; or the disk access time.

* * * * *